April 6, 1965 F. M. SAKIYAMA Plant Pat. 2,491
JUNIPER PLANT
Filed Jan. 9, 1964 2 Sheets-Sheet 1
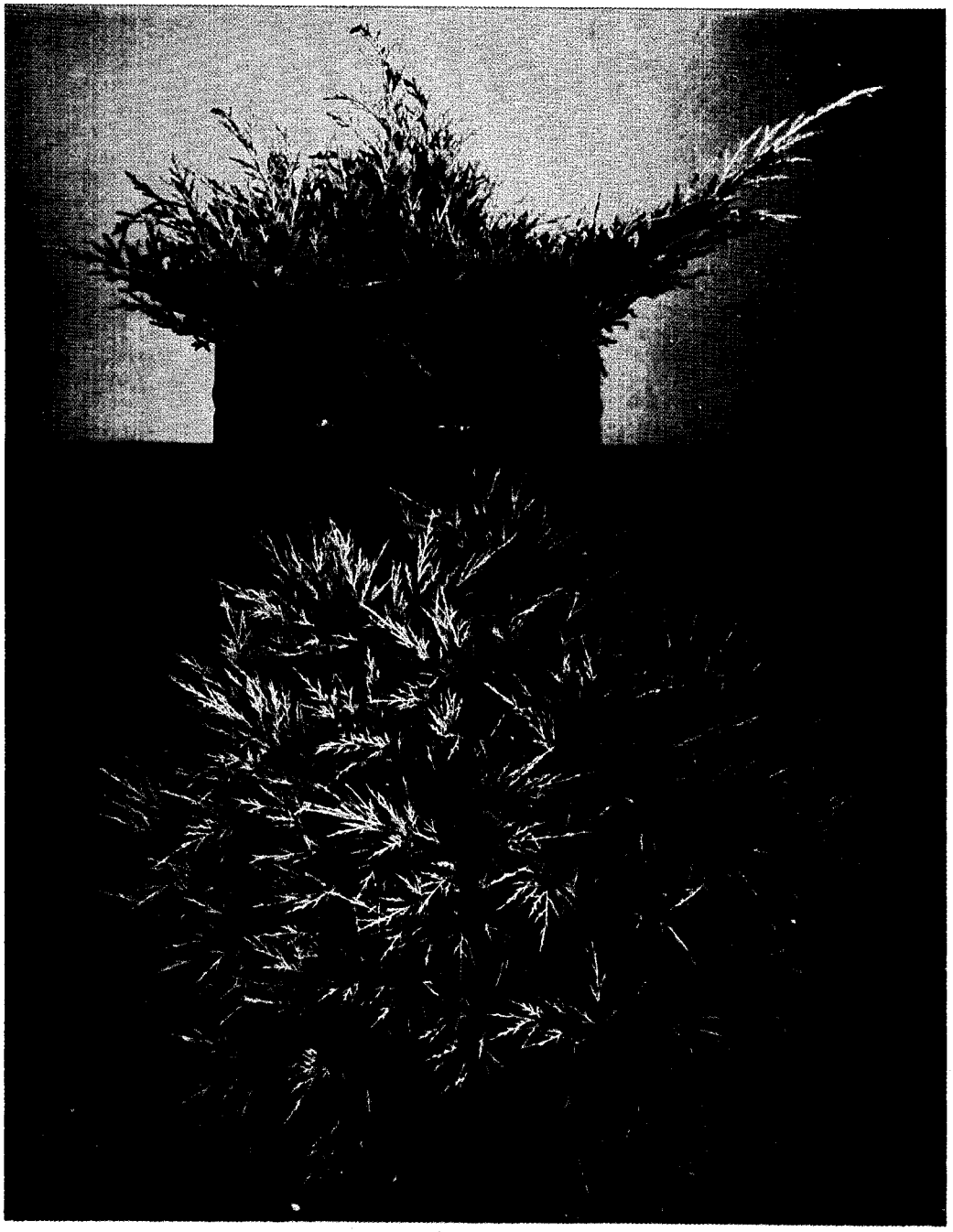
Inventor.
F. M. Sakiyama
By: Robb & Robb
Attorneys.

JUNIPER PLANT
Filed Jan. 9, 1964 2 Sheets-Sheet 2
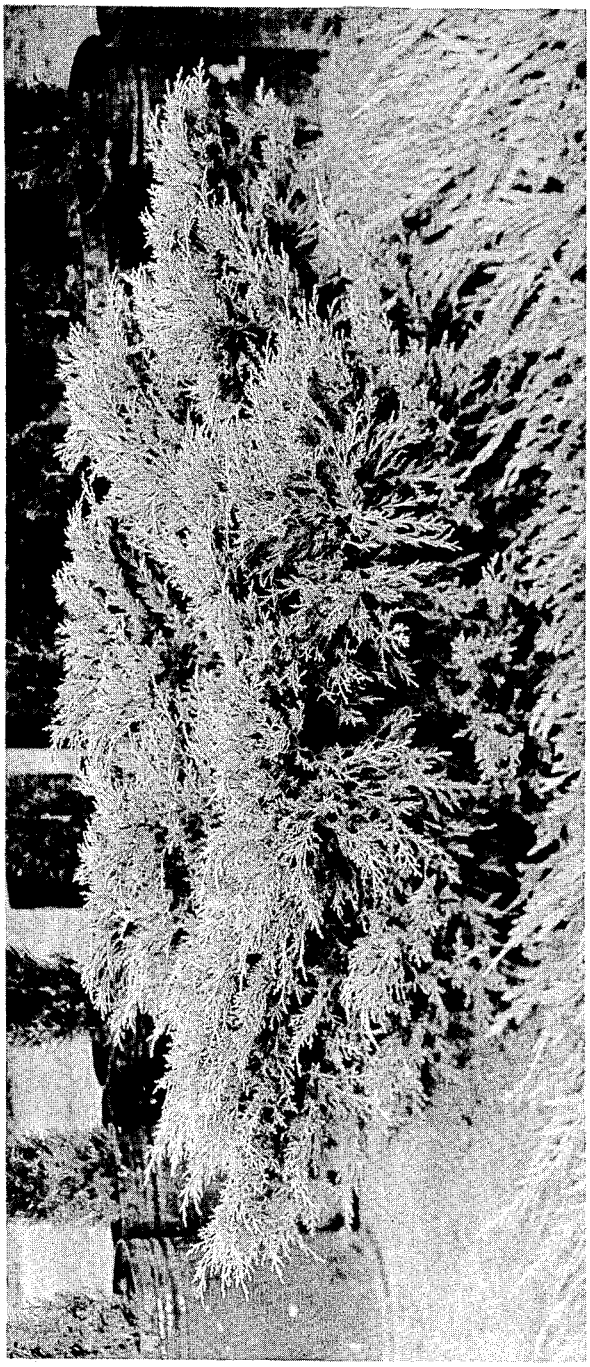
Inventor.
F. M. Sakiyama
By: Robb & Robb
Attorneys.

United States Patent Office

Plant Pat. 2,491
Patented Apr. 6, 1965

2,491
JUNIPER PLANT

Frank M. Sakiyama, 5006 N. Bartlett Ave.,
San Gabriel, Calif.

Filed Jan. 9, 1964, Ser. No. 336,848
1 Claim. (Cl. Plt.—50)

The present invention relates to a new and distinct variety of juniper plant which was discovered by me as a sport of an unnamed and unpatented variety of *Juniperus x media* "pfitzeriana aurea."

At the time of my discovery, I was growing in my nursery at San Gabriel, California, a block of *Juniperus x media* "pfitzeriana aurea," and my attention was attracted to one plant which appeared to be quite different from all of the others in the block. These differences particularly involved the general habits of growth, size, color and other factors. I then succeeded in tracing this plant back to the parent plant from which cuttings had been taken for the plantings in the block aforementioned. Upon close examination of the parent plant, I found thereon a branch which appeared to be identical in all material respects to the branches of the plant which originally attracted my attention. I thereupon made further asexual productions of the new sport, as grown from cuttings planted in my nursery at San Gabriel, and kept the original plants and the reproductions under close observation, and additionally subjected plants to test elsewhere in both southern and northern California. These observations and tests fully confirmed the unusual characteristics of the new sport, as evidenced by the following unique combination of characteristics which are outstanding therein and which distinguish the new sport from its parent, as well as from all other juniper varieties of which I am aware:

(1) Graceful, dwarfish, compact, symmetrical and very lacy habits of growth;

(2) Relatively fine and smooth needle-like foliage;

(3) A distinctive and attractive over-all golden color which becomes richer and darker in cold weather;

(4) A natural only moderately spreading habit which requires little or no trimming or other special attention; and (5) Good temperature tolerance, as evidenced by the fact that plants have stood up well in temperatures ranging from as low as —20° F. to as high as 110° F.

The accompanying drawings show a typical specimen plant as depicted in color, with one of the color views being on a slightly enlarged scale, as well as an additional more mature specimen plant as depicted in black and white to better illustrate the general habits of growth.

The following is a detailed description of my new juniper variety, with color terminology in accordance with Ridgway's Colour Standards and Nomenclature, except where general color terms of ordinary dictionary significance are obvious:

Locality where grown and observed: Sam Gabriel, California.

Propagation: Holds its distinguishing characteristics through succeeding propagations by cuttings.

Plant:

*Form.*—Dwarf; much-branched.

*Habit.*—Upright; symmetrical; closely knit with lacy graceful effect.

*Growth.*—Attains height of about 2 feet and width of about 3 feet at age of about 4 years when grown from a liner plant started in a 2 inch pot.

Blooms: None produced.

Foliage:

*Type.*—Needle shaped.

*Color.*—New foliage: upper side—Pinard Yellow, Plate IV D, with edging of Light Yellow Green, Plate VI D; under side—Scheeles Green, Plate VI I. Mature foliage: upper side—Baryta Yellow, Plate IV F with edging of Light Yellow Green, Plate VI D; under side—Peacock Green, Plate VI I.

*Texture.*—Fairly smooth and somewhat leathery, but not as scaly as parent variety.

*Aspect.*—Graceful; lacy; compact.

*Disease and insect resistance.*—Good, as evidenced by the fact that no disease or insect problems have occurred over a period of several years, even when exposed to aphis and red spider, and requiring no special attention other than usual nursery spraying treatment, as compared with other varieties grown under the same cultural conditions in the same locality at San Gabriel, California.

Hardiness: Good, as evidenced by the fact that the plants have stood up well under temperatures ranging from as low as —20° F. and as high as 110° F.

General observations: Grows well both in ground and in containers and does not tend to spread out of bounds in a short time as do many juniper varieties; its graceful, compact and lacy habits are much more attractive than the habits of the parent variety, and is enhanced by an over-all golden effect without showing yellow where portions of the plant overlap, contrary to the parent variety which is merely splashed with golden color at the tips and tends to grow much taller so as to require heavy trimming which is not necessary in the case of the new sport which is definitely more compact as it spreads to only a moderate extent and does not send out widely spreading roots.

I claim:

A new and distinct variety of juniper plant, substantially as herein shown and described, characterized particularly as to novelty by the unique combination of graceful, dwarfish, compact, symmetrical and very lacy habits of growth, relatively fine and smooth needle-like foliage, a distinctive and attractive over-all golden color which tends to become richer and darker in cold weather, a natural moderately spreading habit, thereby making trimming or pruning unnecessary and requiring no other special attention, and a good temperature tolerance.

No references cited.

T. GRAHAM CRAVER, *Primary Examiner.*

ABRAHAM G. STONE, *Examiner.*